United States Patent [19]
Cortright

[11] Patent Number: 6,033,676
[45] Date of Patent: Mar. 7, 2000

[54] TREATMENT OF SCALP BALDNESS WITH 8-HYDROXYQUINOLINE SULFATE

[75] Inventor: Joyce A. Cortright, Pine Bush, N.Y.

[73] Assignee: Joseph B. Taphorn, Poughkeepsie, N.Y.

[21] Appl. No.: 07/849,191

[22] Filed: Mar. 11, 1992

[51] Int. Cl.[7] ........................................ A61K 7/06
[52] U.S. Cl. ........................ 424/401; 514/880; 424/70.1
[58] Field of Search ........................ 424/401, 70; 514/880

[56] References Cited

U.S. PATENT DOCUMENTS 3,886,277  5/1975  Randebrock ............................ 514/852
4,895,727  1/1990  Allen ...................................... 514/946

OTHER PUBLICATIONS

The Merck Index, p. 770 (1989), 11th ed.

*Primary Examiner*—Thurman K. Page
*Attorney, Agent, or Firm*—Joseph B. Taphorn

[57] ABSTRACT

A process and product restoring hair to bald-headed men involves massaging the scalp with a commercially available ointmenmt known as BAG BALM.

1 Claim, No Drawings

TREATMENT OF SCALP BALDNESS WITH 8-HYDROXYQUINOLINE SULFATE

FIELD OF THE INVENTION

This invention relates to baldness, and more particularly to a method and product for overcoming baldness.

BACKGROUND OF THE INVENTION

Baldness is the absence of hair on the head. Baldness frequently becomes a problem as people age. There is generally gradual thinning of the hair over the head. The top of the head may become completely bald.

Baldness may also be hereditary.

While the causes of baldness are not fully understood, changes in hormone levels, such as that of the male hormone testosterone and/or androsterone, are thought to play a part. Infection may also.

Hair consists of a root and a shaft. The root is a soft bulb, while the rest is the shaft. The root and a section of the shaft below the skin surface lie in a follicle sac. The bottom of the follicle sac projects the papilla which contains an artery that nourishes the root.

The hair grows by forming new cells at the base of the root. The cells form around the nourishing papilla, as the old ones are pushed away and die and became part of the shaft. Human scalp hair usually grows one-half inch per month for two to four years. Then the shaft falls off and a new shaft replaces it. When the old shaft falls off, the papilla becomes active again and new hair appears.

Baldness results when the old shaft is no longer replaced.

SUMMARY OF THE INVENTION

It has been discovered that rubbing the ointment BAG BALM, normally used on cows udders and sometimes on human skin that is chapped or broken, into the scalp of bald-headed men, restores hair growth.

DESCRIPTION OF PREFERRED EMBODIMENTS OF THE INVENTION

The invention involves rubbing-in or massaging the scalp of bald-headed men with an ointment marketed commercially as BAG BALM by the Dairy Association Company, Inc, of Lyndon Wells, Vt. 05851. The BAG BALM packaging indicates that the active ingredient is 8-hydroxy.quinoline Sulfate 0.3% carried in a petrolatum and lanolin base.

The ointment BAG BALM is frequently massaged into cow's udders to relieve a problem believed caused by a hormone release during pregnancy. The harmone causes the animal's bag or udder to become very hard and get what sometimes is called a "plate" in it. Milk flow is impaired. By taking a hot cloth and massaging a quantity of BAG BALM onto the udder a couple of times a day for a few days, the "plate" is broken, the bag softens, and milk comes down to the teats.

BAG BALM is also used on animal skin cuts and scrapes to promote healing.

BAG BALM is also used by some medical people on human skin that is broken and on dry human skin that is chapped.

BAG BALM has been contacted by human hands for years and no adverse effects are know by applicant, a Certified Home Health Aide, to obtain.

Thus in accordance with the invention it is now possible to restore hair growth on bald heads, and with an apparently safe product. It is believed that the rubbed-in ointment offsets the effects of lower levels of male hormones in the papilla and/or provides an antimicrobial effect on infection.

The following examples are submitted to illustrate but not to limit this invention. All parts and percentages in the specification and claims are believed based upon weight.

EXAMPLE 1

Subject had been bald for most (over fifty (50) years) of his adult life, and was in his late seventies, in poor health and with poor circulation. He had an excessively dry spot with broken skin on the top of his scalp which had never really healed thoroughly. BAG BALM was applied, via daily massages, to this dry spot in the hope it would relieve the dry skin. No changes in his medicine were made.

Every morning his scalp was washed with a warm wash cloth. Then it was dried well. After that, about one (1) teaspoon of BAG BALM was thoroughly massaged into the entire bald spot. After a month or so, hair was noticed growing-up out of the scalp. Most of the hair was growing slowly, but on the very top of the head there was some very long hair; six (6) or eight (8) hairs were three (3) to four (4) inches long. There was a lot of short pieces of hair all over. Two (2) months later, during which time BAG BALM was not applied, subject's hair was still growing; he had about three (3) times as much long hair as he did two (2) months earlier. But his scalp was very dry and flaking again. No side effects, other that the hair growth, from using BAG BALM were noticed.

EXAMPLE 2

Subject, a hair dresser in his thirties, had tried many different products on his scalp before he began using BAG BALM. He reports that BAG BALM is the best product he has ever used. After about two (2) months of daily massaging of BAG BALM into his scalp, his bald spot on top of his head was filling-in some. Furthermore, in the front of his head, some hair that had stopped growing, was starting to grow again.

EXAMPLE 3

Another subject, about forty (40) years of age, has been bald for twenty (20) or more years. He picked a spot on his scalp to try the invention. He reports that just after two (2) weeks of daily massage, he has fuzz on that spot and not elsewhere.

GENERAL

Applicant surmises that the active antimicrobial agent, 8-hydroxy.quinoline sulfate, reaches the papilla, and is effective to off-set the male hormones such as testosterone and/or androsterone, and/or kill or seriously weaken any bacteria about or in the papilla and impairing its normal functioning.

Having set forth the general nature and specific embodiments of the method and material of the invention, the true scope is now particularly pointed out in the appended claims.

What is claimed is:

1. The method of treating scalp baldness with an antimicrobial to restore hair growth, which comprises rubbing into the scalp the ointment wherein the active ingredient 8-hydroxy.quinoline sulfate 0.3% is carried in a petrolatum and lanolin base.

* * * * *